United States Patent [19]

Tsuchiya et al.

[11] Patent Number: 5,556,776
[45] Date of Patent: Sep. 17, 1996

[54] SUCRASE GENE DERIVED FROM CORYNEFORM BACTERIA

[75] Inventors: Makoto Tsuchiya; Kiyoshi Miwa, both of Kawasaki, Japan

[73] Assignee: Ajinomoto Co., Inc., Tokyo, Japan

[21] Appl. No.: 311,174

[22] Filed: Sep. 23, 1994

[51] Int. Cl.$^6$ ............... C12P 13/04; C12P 13/14; C12P 13/08; C07H 21/04

[52] U.S. Cl. ............ 435/106; 435/110; 435/115; 435/252.32; 435/320.1; 536/23.2

[58] Field of Search ................. 435/69.1, 110, 435/115, 172.3, 211, 252.32; 536/23.2

[56] References Cited

U.S. PATENT DOCUMENTS 5,284,757  2/1994  Tsuchida et al. ............... 435/114
5,380,657  1/1995  Schaefer et al. ............... 435/172.3

OTHER PUBLICATIONS

Gunasekaran et al. (1990) J. Bacteriol. 172(12): 6727–6735.

*Primary Examiner*—Robert A. Wax
*Assistant Examiner*—Lisa J. Hobbs
*Attorney, Agent, or Firm*—Oblon, Spivak, McClelland, Maier & Neustadt, P.C.

[57] ABSTRACT

The present invention provides a DNA fragment derived from Coryneform bacteria and containing a gene coding for a protein having sucrase activity and a recombinant DNA vector containing said DNA fragment and capable of expression in Coryneform bacteria, The recombinant DNA is introduced into Coryneform bacteria to enhance their sucrase activity, By using the bacteria having enhanced sucrase activity a method is provided for efficiently producing L-amino acids and nucleic acids in a short period of time.

7 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: unknown ( i i ) MOLECULE TYPE: Other nucleic acid ( x i ) SEQUENCE DESCRIPTION: SEQ ID NO:1:

GGGCTGTTAA ATGACCCAAA TGGG                                                    24

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: unknown ( i i ) MOLECULE TYPE: Other nucleic acid ( x i ) SEQUENCE DESCRIPTION: SEQ ID NO:2:

TACATGTGGG AATGCCCTGA TTTG                                                    24

( 2 ) INFORMATION FOR SEQ ID NO:3:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: unknown ( i i ) MOLECULE TYPE: Other nucleic acid ( x i ) SEQUENCE DESCRIPTION: SEQ ID NO:3:

GATCAAGGTT TTGATTTTTA CGCGCCGCAA ACA                                    33

( 2 ) INFORMATION FOR SEQ ID NO:4:

( i ) SEQUENCE CHARACTERISTICS:
        ( A ) LENGTH: 6911 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:4:

AGTCCGTCGA CGCCACCATT GATGTGGTGG TCACCGAGCT TGCGGAGGCT TTCTACATCT    60

ACGCTCCCGT CGGCGTGGAG TGGGGTCATT ACGGGTGGGA TCACGCCGGT GAAAGTTGCG   120

```
GAACCCATGG  TGTTCCTTGT  GGGTTGAGGG  AACGAGTGCG  GGTGAGAAGT  TTTTCAAGTG   180
TCTGCAGTTT  TTAAGTTATG  CATCATCAGC  TTGGAAGGCT  GAGGTAATTC  AGTAGACCTG   240
CAACAGCAGG  CCTCAAGTCC  GAAGATAATT  AACCTAGATC  CGTAGACATA  AGACATCATA   300
CGTCCTATGC  TTGCTGGAAG  GAACCAAATA  ACCTCAGAAA  GATGGCAGAA  GTGGTGCATT   360
ATCAAGAAAA  TGCAGGTCAA  GCAGTTAAAA  AAATTGAGGG  AAGAATTGTT  CCCCCCCTCG   420
GGGTGATTGA  TGGCTTTCTC  CAACTCGAAA  ACGGCATCAT  CACGGAACTC  TCTGGAGAAC   480
CAGCACCTAA  AAACGCAGGA  TTCCACCCCG  AACTCCCCAC  GATTGTTCCC  GGTTTTATTG   540
ATCTTCATAA  TCACGGTGGA  AACGGTGGCG  CGTTCCTAC   GGAACGCAG   GACCAGGCGA   600
GGAACACCGC  GCAGTATCAC  CGCGAACATG  GCACGACCGT  GATGTTGCCA  AGCATGGTTT   660
CGGCGCCGGC  TGACGCACTG  GCAGCGCAGG  TGGAAAACCT  TATTCCCTTG  TGTGAAGAGG   720
TCCTGCTGTG  CGGCATTCAC  CTCGAGGGCC  CTTTCATCAA  CGCATGCCGT  TGTGGTGCTC   780
AAAACCCGGA  TTTCATTTTT  CCCGGCAACC  CAACAGATCT  TGCCCGGGTG  ATCCATGCGG   840
GAAAAGGTTG  GATCAAATCG  ATCACAGTAG  CGCCGGAAAC  TGACAATCTT  TCTGAGCTTC   900
TCGATCTCTG  CGCAGCGCAC  CACATCATTG  CTTCCTTCGG  GCACACTGAT  GCAGATTTTG   960
ATACCACTAC  CAGCGCAATT  GCCTTGGCTA  AAGAGAAAAA  TGTGACGGTC  ACGGCTACGC  1020
ATTTGTTCAA  TGCGATGCCT  CCGCTGCATC  ATAGGGCTCC  CGGCAGCGTG  GGCGCTTTGC  1080
TTGCTGCGGC  ACGTGCCGGG  GACGCATATG  TTGAGTTGAT  CGCCGACGGC  GTGCATTTGG  1140
CCGATGGAAC  GGTCGATCTA  GCTCGTTCCA  CAACGCCTT   TTTCATCACG  GACGCCATGG  1200
AAGCCGCCGG  AATGCCAGAC  GGTGAGTACA  TTTTGGGCGT  TTTGAACGTC  ACCGTCACCG  1260
ATGGAGTCGC  CCGTCTGCGC  GATGGCGGCG  CCATCGCCGG  GGCACCAGC   ACACTAGCGA  1320
GTCAGTTCGT  GCACCACGTG  CGCAGGGGTA  TGACGCTTAT  CGACGCGACC  CTCCACACCT  1380
CAACCGTCGC  CGCTAAAATT  CTCGGTCTTG  GCGATCACGA  AATCGCTAAA  TCCAACCCTG  1440
CAAATTTTGT  GGTCTTTGAC  TCAAACGGCC  AGGTGCAAAA  GGTCCATTTA  GGTCATCAAG  1500
TACTTTAAGT  ACGAGTAAAA  CTATCCTGAT  TTTAAGGAG   TCCACCATG   GAAATCACTA  1560
TCTGCAAAGA  CGAGCAAGAA  GTCGGCAAAG  CAGTTGCAGT  CCTAATCGCA  CCCTTCGCCA  1620
ACAAGGGTGG  AACCTTGGGG  CTTGCAACAG  GATCCTCACC  ACTGAGTACC  TACCAAGAGC  1680
TCATTCGCAT  GTATGAAGCT  GGGGAAGTGT  CATTCAAGAA  CTGCAAGGCA  TTCTTGTTGG  1740
ATGAATACGT  GGGACTAACC  CGTGACGATG  AAAACAGCTA  CTTTAAAACC  ATTCGCAAAG  1800
AGTTCACTGA  CCACATCGAC  ATCGTTGATG  AAGAGGTCTA  CAGCCCAGAT  GGTGCAAACC  1860
CTGATCCATA  CGAAGCAGCT  GCAGAGTATG  AGGCAAAGAT  CGCTGCAGAA  TCCGTTGAAG  1920
TTCAAATCCT  TGGCATCGGC  GGAAACGGCA  CATCGCTTTC  ATTGAACCAT  CATCTTCTCT  1980
GTCAGGACTG  ACAAAGGTCC  AGGCGCTGCA  CCCTAAAACT  GTGGAGGACA  ACGCTCGATT  2040
CTTCAACACC  ATCGAAGAGG  TCCCAACCCA  CGCCGTCACC  CAGGGTTTGG  CACTTTGTC   2100
CCGCGCGCAA  ACATCGTGT   TGGTGGCAAC  TGGTGAAGGA  AAAGCCGACG  CCATCCGCGG  2160
AACTGTGGAA  GGCCCAGTGA  CTGCTTCTTG  CCCAGGTTCC  ATCCTGTAGA  TGCACAACAT  2220
GCCACCATCA  TCGTTGGATG  AAGCAGCAGT  ATCCAAGCTG  GAAAACGCTG  ATCACTACCG  2280
TCTCATGGAG  CAATTAAAGC  TGCGCTAGAA  ACAAAAAGGA  AAGTACTGTG  TGGGGCTATG  2340
CACACAGAAC  TTTCCAGTTT  GCGCCCTGCG  TACCATGTGA  CTCCTCCGCA  GGGCAGGCTC  2400
AATGATCCCA  ACGGAATGTA  CGTCGATGGA  GATACCCTCC  ACGTCTACTA  CCAGCACGAT  2460
CCAGGTTTCC  CCTTCGCACC  AAAGCGCACC  GGCTGGGCTC  ACACCACCAC  GCCGTTGACC  2520
```

```
GGACCGCAGC  GATTGCAGTG  GACGCACCTG  CCCGACGCTC  TTTACCCGGA  TGCATCCTAT    2580
GACCTGGATG  GATGCTATTC  CGGTGGAGCC  GTATTTACTG  ACGGCACACT  TAAACTTTTC    2640
TACACCGGCA  ACCTAAAAAT  TGACGGAAAG  CGCCGCGCCA  CCCAAAACCT  TGTCGAAGTC    2700
GAGGACCCAA  CTGGGCTGAT  GGGCGGCATT  CATCGCCGTT  CGCCTAAAAA  TCCGCTTATC    2760
GACGGACCCG  CCAGCGGTTT  CACACCCCAT  TACCGCGATC  CCATGATCAG  CCCTGATGGT    2820
GATGGTTGGA  ACATGGTTCT  TGGGGCCCAA  CGCGAAAACC  TCACCGGTGC  AGCGGTTCTA    2880
TACCGCTCGA  CAGATCTTGA  AAACTGGGAA  TTCTCCGGTG  AAATCACCTT  TGACCTCAGT    2940
GATGCACAAC  CTGGTTCTGC  TCCTGATCTC  GTTCCCGATG  GCTACATGTG  GAATGCCCC     3000
AACCTTTTTA  CGCTTCGCGA  TGAAGAAACT  GGCGAAGATC  TCGACGTGCT  GATTTTCTGT    3060
CCACAAGGAT  TGGACCGAAT  CCACGATGAG  GTTACTCACT  ACGCAAGCTC  TGACCAGTGC    3120
GGATATGTCG  TCGACAAGCT  TGAAGGAACG  ACCTTCCGCG  TCTTGCGAGG  ATTCAGCGAG    3180
CTGGATTTCG  GCCATGAATT  CTACGCACCG  CAGGTTGCAG  TAAACGGTTC  TGATGCCTGG    3240
CTCGTGGGCT  GGATGGGGCT  GCCCGCGCAG  GATGATCACC  CAACAGTTGC  ACAGGAAGGA    3300
TGGGTGCACT  GCCTGACTGT  GCCCCGCAAG  CTTCATTTGC  GCAACCACGC  GATCTACCAA    3360
GAGCTCCTTC  TCCCAGAGGG  GGAGTCGGGG  GTAATCAGAT  CTGTATTAGG  TTCTGAACCT    3420
GTCCGAGTAG  ACATCCGAGG  CAATATTTCC  CTCGAGTGGG  ATGGTGTCCG  TTTGTCTGTG    3480
GATCGTGATG  GTGATCGTCG  CGTAGCTGAG  GTAAACCTG   GCGAATTAGT  GATCGCGGAC    3540
GATAATACAG  CCATTGAGAT  AACTGCAGGT  GATGGACAGG  TTTCATTCGC  TTTTCCGGGC    3600
CTTCAAAGGT  GACACTATTG  AGAGATAAGT  CATATAAAAG  GGTCTTTTGT  GGCGAATTGT    3660
ACAAATACTT  CGCAAAATCC  CTTGATCTAG  TTATTGTCAC  TGATGACAAC  CCTCGTTCAG    3720
AGGTGCCTGC  CACGATTCGC  GCAGCAGTCA  CTGCAGGAGC  ACAGCAGGGT  GCTTCAGAGT    3780
CCGAACGACC  GGTGGAAGTC  CTAGAAATTG  GTGACCGTGC  AGAAGCAATT  CGCGTTTTGG    3840
TCGAGTGGGC  ACAGCCTGGA  GATGGCATTG  TAGTAGCTGG  AAAAGGCCAT  GAAGTTGGAC    3900
AACTAGTTGC  TGGTGTCACC  CACCATTTTG  ATGACCGCGA  AGAAGTTCGC  GCTGCTTTGA    3960
CAGAAAAGCT  CAACAATAAA  CTTCCCCTTA  CTACGGAAGA  AGGATAGGCC  ACAGTCATGA    4020
TCACAATGAC  CCTTGGGGAA  ATCGCTGACA  TCGTTGGAGG  CAGGCTTACT  GGCGGTGCTC    4080
AAGAAGATAC  GCTTGTGAGC  TCCAGCGTGG  AATTTGATTC  TCGATCCCTC  ACACCGGGTG    4140
GCTTGTTTTT  AGCACTTCCG  GGTGCTCGTG  TAGACGGGCA  TGATTTTGCT  GCAACTGCAA    4200
TTGAGAAAGG  TGCGGTCGCA  GTATTGGCAG  CCCGTGAGGT  TGACGTACCT  GCGATCGTCG    4260
TGCCTCCAGT  AAAAATCCAG  GAATCCAATG  CTGACATTTA  TGCTCATGAT  CCAGATGGGC    4320
ATGGCGCGGC  GGTAGTGGAG  GCGTTGGTCT  CGGTTGGCTC  GCCACGTGGT  GGATATCTGC    4380
GTGGATGGCC  ATCAATTGAA  CGTTGTGGCT  ATTACTGGTT  CTGTGGGAAA  GACTTCTATG    4440
AAGGATTTCA  TCGCGACGGT  TCTTGGCCAA  GATGGGCCAA  CTGTGGCTCC  TCCGGGCTCG    4500
TTTAACAATG  AGCTTGGTTT  GCCACACACC  GCGCTCCGCT  GCACAACCGA  TACTAAGTAT    4560
TTGGTGGCTG  AGATGTCCGC  GCGTGGCATT  GGACATATTA  AGCACCTGAC  AGAGATTGCT    4620
CCGCCACGGA  TTGCAGCTGT  GCTCAACGTC  GGCCATGCGC  ACCTGGGTGA  ATTTGGATCC    4680
CGCGAGAATA  TCGCGCAGGC  AAAAGGCGAG  ATCATTGAAG  CGCTGCCCTC  GAAGAAAACG    4740
GGTGGGGTAG  CAGTCCTTAA  CGCTGACGAT  CCTTTTGTCG  CCCGGATGGC  TCCACGCACT    4800
AAGGCGCGCG  TGGTGTGGTT  TACCACCGAT  GCAGGTCAAG  CAAAAAAGTC  TGATTATTGG    4860
GCAACGAGTA  TTTCACTGGA  CGCTGTTGCG  CGGGCAAGCT  TTACGCTGAA  CACGAAGGAC    4920
```

```
GGGTCTTGGC CGGTCGCCCT GCAGGTTTTT GGTGAGCACC AGGTTGCTAA TGCACTTGCT    4980
GCTGCTGCCA TTGCCATGGA AGCTGGCGTC GCCCAGAAT  TGGTGGTTGC TGGATTGGAA    5040
GCACATTCAG CGGCTTCCGC GCACCGCATG GATGTAAAGA CCCGCGCCGA CGGCGTGACC    5100
ATCATCAACG ATTCTTACAA CGCGAATCCT GATTCTATGC GTGCAGGTAT CGCGGCTCTT    5160
GCGTACACAG CTAGTGGTCG TTCTCTGAAG CAACAAGCTG GGCAGTGCTT GGTCAAATGG    5220
GTGAGCTTGG CGATGACGCC TCGGAAGCCC ATGCCGAACT TGGTGCTGAG CTGCCTAAAT    5280
ACAATGTTCA AGAACTTGTC GCAGTGGGGG AGAACCCTAC CTGTGCAGCA CTTGCAGAGT    5340
CCGCAGCGAG CCTGGGTGTG AGTACTCACG TAGTTTCAGA CGTTGATGCA GCGCTCGAGT    5400
TGCTCGCAGC CCATATTAAG CGGGATGATG TAGTGCTGGT TAAGGCTTCA AATGCTGATC    5460
GCCTGTGGAG GGTCGCAGAA GCACTACATG GCATGGTGCC GGCCTCAAAA ACACAGGTGG    5520
CTCGGTCAAC GACGATTCTC GTCGGAACGT GGAAGGACAG TAGAAAACAA TGCAACAGAT    5580
TATGGTCAGT GGAACGGTTG CGTTCCTCGT CTCAATCTTT CTCACCCCGG TGTTGATCCG    5640
TTATTTCACT AACCGCCAGT TGGGCCAGGA AATCCGTGAA GAAGGCCTGC AGTCTCACTT    5700
GCGTAAGCGT GGCACTCCAA CCATGGGTGG CATTGCGATT ATCGCGGGCA TTGTTGTGGC    5760
CTATGTGTTT ACCAATATCT TGGCCATGAT CCAAGGCGTT GGTGGATTCA CAGTCTCCGG    5820
CTTGCTCGTG TTGGGTCTGA CCTTGGGCCT TGGTGCCACT GGCTTCGCCG ATGACTTCAT    5880
CAAGCTGTAC ATGAACCGAA ACCTTGGTTT GAACAAGACC GCTAAGCTGG TGTCTCAGCT    5940
GGCCATTGCG TTGATCTTTG GTTTTTGGT  ACTGCAGTTT CCCGATGAAA ACGGTCTGAC    6000
CCCAGCATCA ACCCACCTGT CATTCATTCG CGATATCGAC ACCATTGACC TTGGCTTCGG    6060
GGACAGCGTT TTTGGCATCA TCGTGTTCCT CATTTTTATC TACGTTGTGG TCAGCGCGTG    6120
GTCGAATGCC GTGAACATCA CTGATGGTTT GGATGGTTTG GCTGCAGGTA CCACAGCATT    6180
TGTCATGGGT GCTTACACCT TGATCACGTT CTGGCAGTTC CGAAACTCCT GCGATACTGC    6240
AGTGGAAGCG GGTTGCAATA CGGTGCGTGA TCCACTGGAT TTGTCTGTGT TGTGCGCTGC    6300
TGGTCTGGCG CCACCTTGGG CTTTCTGTGG TGGAATGCGG CACCGACAAA GATCTTCATG    6360
GGCGATACTG GTTCTTTGGC ACTGGGCGGT TTGGTTGCAG GTATTTCTGT GGTTAGCCGC    6420
ACCGAGCTGC TCATGGTTAT CATCGGCGCG CTGTTTGTCA TTGAGGTCGC TTCTGTTGCG    6480
ATCCAGATCG GCGTGTTTAA GACCCGCGGT AAGCGTGTGT TCAAAATGGC TCCGATCCAC    6540
CACCACTTCG AGGCCCTTGG GTGGACTGAA ACTACCGTGA CCATCCGTTT CTGGCTGATC    6600
ACGATCATGA CTGTGTTGGC GGGTGTCGGT GTGTTAACA  GCGACTGGCT CCACTTAGCG    6660
GAGGTATAAA TAATTATGGT TTCTCTGTCC CATTTACCTC AGGCGCTGCA GGGCCGTATT    6720
CTTGTGGCCG GCGCTGGTGT TTCCGGCCTG TCCATAGCAA AGATGCTCAG TGAGTTGCAT    6780
TGCGATGTTG TGGTCACCGA CGAGAACGAA ACTGCACGTC ACATGCTCAT TGAAGTAGTA    6840
GACGTTGCAG ATATCAGCAC CGCCCAGGCT CAGGAACAGC TGGATTCTTT CTCCATTGTG    6900
GTCACCTCCC C                                                        6911
```

1

SUCRASE GENE DERIVED FROM CORYNEFORM BACTERIA

BACKGROUND OF THE INVENTION

1. Field of the Invention

The present invention relates to a sucrase gene derived from Coryneform bacteria. More particularly, the present invention relates to a DNA fragment derived from Coryneform bacteria and containing a gene coding for a protein having sucrase activity, a recombinant DNA obtained by inserting said DNA fragment into a vector capable of expression in Coryneform bacteria, a microorganism belonging to Coryneform bacteria harboring said recombinant DNA and capable of producing an L-amino acid or a nucleic acid, and a method for production of an L-amino acid or a nucleic acid by culturing said microorganism.

2. Discussion of the Background

Many studies have heretofore been reported regarding L-amino acid-producing microorganisms prepared using gene engineering technology. See Biotechnology Letters, Vol. 2, pp. 525–530 (1980); Appl. Environ. Microbiol., Vol. 144, pp. 181–190 (1979); and Preprint of Discussions and Lectures in the Agricultural and Chemical Society of Japan (1981), pp. 8, all incorporated herein by reference. These studies all concern the amplification of genes for the biosynthesis of L-amino acids, thereby increasing per cell productivity for the intended L-amino acids. The amplification does not increase the efficiency of L-amino acid production by enhancing the assimilation of saccharides, the raw materials to be fermented, by the microorganism.

There are some examples referring to the enhancement of the assimilation of saccharides by L-amino acid-producing microorganisms, using gene engineering technology. See Japanese Patent Application Laid-open Nos. 61-119185 and 2-171178 incorporated herein by reference. According to these studies, *Escherichia coli* was provided with the ability to assimilate sucrose by gene manipulation. In particular, a strain of *Escherichia coli* was provided with sucrose uptake activity, later hydrolyzing the sucrose into glucose and fructose, with the result that the strain was capable of utilizing sucrose as a carbon source, an ability which the strain did not possess inherently. No one has reported similar success with Coryneform bacteria, however, and no publication regarding the enhanced ability of Coryneform bacteria to assimilate saccharides such as sucrose, etc., using gene engineering technology has yet appeared.

OBJECTS OF THE INVENTION

One object of the present invention is to improve the sucrose assimilating ability of bacteria of the Coryneform group, by means of gene engineering technology, to thereby increase the speed of fermentation with the altered bacteria and so as to improve the productivity of L-amino acids and nucleic acids from raw materials containing sucrose. More particularly, the objects of the present invention include obtaining a DNA fragment derived from Coryneform bacteria and containing a gene coding for a protein having sucrase activity, a recombinant DNA comprising said DNA fragment, a vector capable of gene amplification in Coryneform bacteria comprising said fragment, a microorganism, particularly a Coryneform bacteria, harboring said recombinant DNA, a microorganism, particularly a Coryneform bacteria, harboring said vector, and a method for improving the efficiency of L-amino acid or a nucleic acid production by fermentation of transformed microorganism, particularly transformed Coryneform bacteria, in the presence of raw materials containing sucrose.

DETAILED DESCRIPTION OF THE PREFERRED EMBODIMENT

The present inventors have succeeded in obtaining the above objects and more by discovering DNA fragments derived from Coryneform bacteria and containing a gene coding for a protein having sucrase activity. In addition, they have discovered a method for producing L-amino acids and nucleic acids in high yield and/or in a shorter period of time than conventional methods by culturing Coryneform bacteria into which recombinant DNA containing the DNA fragment described above had been introduced.

Specifically, the present invention provides a DNA fragment derived from Coryneform bacteria and containing a gene coding for a protein having sucrase activity, a vector capable of gene amplification in Coryneform bacteria and comprising said DNA fragment, a microorganism belonging to Coryneform bacteria harboring said vector and capable of producing an L-amino acid or a nucleic acid, a recombinant DNA obtained by inserting said DNA fragment into a vector capable of gene amplification in Coryneform bacteria and a method for the production of an L-amino acid or a nucleic acid comprising culturing said microorganism.

The term "protein having sucrase activity" as used herein refers to a protein capable of hydrolyzing sucrose to produce glucose and fructose. The protein preferably has a sucrase activity of at least 1 unit/mg of protein, preferably an activity of 2, 3, 4, or 5 or more units/mg of protein.

The term "Coryneform bacteria" as referred to herein indicates aerobic gram-positive rods belonging to the genus Microbacterium, Brevibacterium or Corynebacterium as described in Bergey's manual of Determinative Bacteriology, 8th Ed., p. 599 (1974), incorporated herein by reference, and includes the following wild strains capable of producing L-glutamic acid and mutant strains derived therefrom:

| | |
|---|---|
| *Corynebacterium acetoacidophilum* | ATCC 13870 |
| *Corynebacterium acetoglutamicum* | ATCC 15806 |
| *Corynebacterium callunae* | ATCC 15991 |
| *Corynebacterium glutamicum* | ATCC 13032 |
| *Corynebacterium glutamicum* | ATCC 13060 |
| *Brevibacterium divaricatum* | ATCC 14020 |
| *Brevibacterium lactofermentun* | ATCC 13869 |
| *Corynebacterium lilium* | ATCC 15990 |
| *Corynebacterium melassecola* | ATCC 17965 |
| *Brevibacterium saccharolyticum* | ATCC 14066 |
| *Brevibacterium immariophilum* | ATCC 14068 |
| *Brevibacterium roseum* | ATCC 13825 |
| *Brevibacterium flavum* | ATCC 13826 |
| *Brevibacterium thiogenitalis* | ATCC 19240 |
| *Microbacterium ammoniaphilum* | ATCC 15354 |
| *Brevibacterium ammnoniagenes* | ATCC 6872 |
| *Corynebacterium equi* | ATCC 21280 |

The gene coding for a protein having sucrase activity as referred to herein indicates a gene which codes for a protein having the above described activity for hydrolyzing sucrose to produce glucose and fructose. Sucrase activity is important for microorganisms when they utilize sucrose as a carbon source. The gene is not otherwise limited. Certain preferred base sequences identified herein do not define the scope of this invention. The preferred base sequences, their functional equivalents, particularly those having up to ±300 additional or fewer bases, 3' or 5' or both, as compared to the preferred sequences as well as the ability to code for a protein having at least 75% of the sucrase activity that the protein coded for by the preferred sequence exhibits, and any other gene meeting the above functional requirements are included herein.

To obtain a DNA fragment containing a gene coding for a protein having sucrase activity according to the present invention, a method comprising construction of a gene library from chromosomal DNA of Coryneform bacteria may be used followed by the cloning of a sucrase gene by hybridization. This will be described in detail hereunder.

A gene library of the Coryneform genome can be constructed using conventional techniques such as those discussed by Sambrook et al, Molecular Cloning: A laboratory manual, 2nd ed., CSH press, NY, 1989 incorporated herein by reference, particularly chapters 1 and 9. Briefly, chromosomal DNA obtained from Coryneform bacteria is partially digested with a restriction endonuclease, ligated into a suitable cloning vector such as a plasmid and transformed into a suitable host. A preferred cloning vector for construction of the Coryneform genomic library is pUC18. A preferred host is *E.coli*, particularly *E.coli* JM109.

Sucrase or invertase genes have been cloned with *Bacillus subtilis* (Gene, Vol. 45, pp. 221–225 (1986) incorporated herein by reference), *Zymomonas mobilis* (J. Bacteriol., Vol. 172, pp. 6727–6735 (1990) incorporated herein by reference), *Streptococcus mutans* (Infect. Immun., Vol. 56, pp. 1956–1960 (1988) incorporated herein by reference), yeasts of the genus Saccharomyces (Nucleic Acids Res., Vol. 11, pp. 1943–1954 (1983) incorporated herein by reference), *Vibrio alginolyticus* (Gene, Vol. 80, 49–56 (1989) incorporated herein by reference), etc., and these genes are homologous to one another in some degree (J. Bacteriol., Vol. 172, pp. 6727–6735 (1990) incorporated herein by reference). Synthetic DNAs can be prepared, using conventional means such as solution or solid phase DNA synthesis preferably using an automated DNA synthesizer, on the basis at the portions common to these microorganisms.

These synthetic DNAs thus formed are phosphorylated, for example by using [$\gamma$-$^{32}$P]ATP as the substrate, to prepare labeled probes. The library formed above is then screened via colony hybridization using the probes. From the colonies hybridizing with the probes, those expressing sucrase activity are selected. The active DNA fragment is then excised from the cloning vector by conventional techniques.

The expression vector comprising the DNA fragment containing a gene coding for a protein having sucrase activity, which is employed in the present invention, is not specifically limited but, in general, may be any plasmid derived from Coryneform bacteria. For example, useful vectors include pHM1519 (Agric., Biol. Chem., Vol. 48 (1984), pp. 2901–2903 incorporated herein by reference), pAM330 (Agric. Biol· Chem., Vol. 48 (1984), pp. 2901–2903 incorporated herein by reference), drug-resistant plasmids based on these, etc. The vector may be introduced in chromosomes by homologous recombination.

Specific examples of Coryneform bacteria which are used as the host bacteria in the present invention include wild strains of L-glutamic acid-producing bacteria and mutant strains derived therefrom and capable of producing another L-amino acid or a nucleic acids such as inosine, 5'-inosinic acid, guanosine and 5'-guanylic acid. The L-amino acids include those produced by Coryneform bacteria, including, for example, L-glutamic acid, L-lysine, L-threonine, L-aspartic acid, L-isoleucine, L-arginine, L-proline, L-histidine, L-valine, L-leucine, L-phenylalanine, L-glutamine, etc.

Specific examples of hosts which are suitable for producing various L-amino acids and nucleic acids are mentioned below.

(i) Hosts preferred for producing L-glutamic acid:,

*Brevibacterium lactofermentum* AJ 12745 (FERM BP-2922); see U.S. Pat. No. 5,272,067, page 561.

*Brevibacterium lactofermentum* AJ 12746 (FERM BP-2923): see U.S. Pat. No. 5,272,067.

*Brevibacterium lactofermentum* AJ 12747 (FERM BP-2924); see U.S. Pat. No. 5,272,067.

*Brevibacterium lactofermentum* AJ 12748 (FERM BP-2925); see U.S. Pat. No. 5,272,067.

*Corynebacterium glutamicum* ATCC 21942; see Japanese Patent Application Laid-Open No. 5-3793, page 3, Table 1.

In addition to these and others, wild strains of Coryneform bacteria mentioned below can also be employed as a host.

| | |
|---|---|
| *Corynebacterium acetoacidophilum* | ATCC 13870 |
| *Corynebacterium acetoglutamicum* | ATCC 15806 |
| *Corynebacterium callunae* | ATCC 15991 |
| *Corynebacterium glutamicum* | ATCC 13032 |
| *Corynebacterium glutamicum* | ATCC 13060 |
| *Brevibacterium divaricatum* | ATCC 14020 |
| *Brevibacterium lactofermentum* | ATCC 13869 |
| *Corynebacterium lilium* | ATCC 15990 |
| *Corynebacterium melassecola* | ATCC 17965 |
| *Brevibacterium saccharolyticum* | ATCC 14066 |
| *Brevibacterium immariophilum* | ATCC 14068 |
| *Brevibacterium roseum* | ATCC 13825 |
| *Brevibacterium flavum* | ATCC 13826 |
| *Brevibacterium thiogenitalis* | ATCC 19240 |
| *Microbacterium ammoniaphilum* | ATCC 15354 |

(ii) Hosts preferred for producing L-lysine:

*Brevibacterium lactofermentum* AJ 12031 (FERM BP-277); see Japanese Patent Application Laid-Open No. 60-62994, page 525, left bottom column.

*Brevibacterium lactofermentum* ATCC 39134; see Japanese Patent Application Laid-Open No. 60-62994, page 473, right bottom column.

*Brevibacterium lactofermentum* AJ 11082 (NRRL B-11470, FERM P-3840); see U.S. Pat. No. 4,275,157

*Brevibacterium lactofermentum* AJ 12435 (FERM BP-2294); see U.S. Pat. No. 5,304,476

*Brevibacterium lactofermentum* AJ 12592 (FERM BP-3239); see U.S. Pat. No. 5,304,476

*Brevibacterium lactofermentum* AJ 12593 (FERM BP-3240); see U.S. Pat. No. 5,304,476

*Corynebacterium glutamicum* AJ 12596 (FERM BP-3242); see U.S. Pat. No. 5,304,476

*Corynebacterium glutamicum* AJ 3463 (FERM P-1987); see Japanese Patent Publication No. 51-34477.

(iii) Hosts preferred for producing L-threonine:

*Brevibacterium lactofermentum* AJ 11188 (FERM P-4190); see Japanese Patent Application Laid-Open No. 60-87788, page 473, right top column.

*Corynebacterium glutamicum* AJ 11682 (FERM BP-118); see Japanese Patent Publication No. 2-31956, page 230, column 8.

*Brevibacterium flavum* AJ 11683 (FERM BP-119); see Japanese Patent Publication No. 2-31956, page 231, column 10.

(iv) Hosts preferred for producing L-aspartic acid:

*Brevibacterium flavum* AJ 3859 (FERM P-2799); see Japanese Patent Application Laid-Open No. 51-61689, page 524, left top column.

*Brevibacterium lactofermentum* AJ 3860 (FERM P-2800); see Japanese Patent Application Laid-Open No. 51-61689, page 524, left top column.

*Corynebacterium acetoacidophilum* AJ 3877 (FERM P-2803); see Japanese Patent Application Laid-Open No. 51-61689, page 524, left top column.

*Corynebacterium glutamicum* AJ 3876 (FERM P-2802); see Japanese Patent Application Laid-Open No. 51-61689, page 524, left top column.

(v) Hosts preferred for producing L-isoleucine:

*Brevibacterium lactofermentum* AJ 12404 (FERM P-10141) (see Japanese Patent Application Laid-Open No. 2-42988, page 603, left bottom column).

*Brevibacterium flavum* AJ 13405 (FERM P-10142) (see Japanese Patent Application Laid-Open No. 2-42988, page 524, left bottom column).

(vi) Hosts preferred for producing L-arginine:

*Brevibacterium flavum* AJ 12144 (FERM P-7642); see Japanese Patent Publication No. 5-27388, page 174, column 4.

*Corynebacterium glutamicum* AJ 12145 (FERM P-7643); see Japanese Patent Publication No. 5-27388, page 174, column 4.

*Brevibacterium flavum* ATCC 21493; see Japanese Patent Application Laid-Open No. 5-3793, page 3, Table 1.

*Corynebacterium glutamicum* ATCC 21659; see Japanese Patent Application Laid-Open No. 5-3793, page 3, Table 1.

(vii) Hosts preferred for producing L-proline:

*Brevibacterium lactofermentum* AJ 11225 (FERM P-4370); see Japanese Patent Application Laid-Open No. 60-87788, page 473, left top column.

*Brevibacterium flavum* AJ 11512 (FERM P-5332); see Japanese Patent Publication No. 62-36679, page 185, column 2.

*Brevibacterium flavum* AJ 11513 (FERM P-5333); see Japanese Patent Publication No. 62-36679, page 185, column 2.

*Brevibacterium flavum* AJ 11514 (FERM P-5334); see Japanese Patent Publication No. 62-36679, page 185, column 2.

*Corynebacterium glutamicum* AJ 11522 (FERM P-5342); see Japanese Patent Publication No. 62-36679, page 185, column 2.

*Corynebacterium glutamicum* AJ 11523 (FERM P-5343); see Japanese Patent Publication No. 62-36679, page 185, column 2.

(viii) Hosts preferred for producing L-histidine:

*Brevibacterium flavum* AJ 3420 (FERM P-2316); see U.S. Pat. No. 5,294,547

*Brevibacterium flavum* AJ 12425 (FERM BP-2212); see U.S. Pat. No. 5,294,547

*Corynebacterium glutamicum* AJ 12092 (FERM P-7273); see U.S. Pat. No. 5,294,547

*Corynebacterium glutamicum* AJ 12426 (FERM BP-2213); see U.S. Pat. No. 5,294,547

(ix) Hosts preferred for producing L-valine:

*Brevibacterium lactofermentum* AJ 3434 (FERM P-1845); see U.S. Pat. No. 5,188,948

*Brevibacterium lactofermentum* AJ 12341 (FERM BP-1763); see U.S. Pat. No. 5,188,948

*Corynebacterium glutamicum* AJ 3776 (FERM P-2601); see U.S. Pat. No. 5,188,948

*Corynebacterium glutamicum* AJ 12342 (FERM BP-1764); see U.S. Pat. No. 5,188,948

(x) Hosts preferred for producing L-leucine:

*Brevibacterium lactofermentum* AJ 3452 (FERM P-1965); see U.S. Pat. No. 3,970,519

*Brevibacterium lactofermentum* AJ 3719 (FERM P-2517); see U.S. Pat. No. 3,970,519

*Corynebacterium glutamicum* AJ 3453 (FERM P-1966); see U.S. Pat. No. 3,970,519

*Corynebacterium glutamicum* AJ 3455 (FERM P-1968); see U.S. Pat. No. 3,970,519

(xi) Hosts preferred for producing L-phenylalanine:

*Brevibacterium lactofermentum* AJ 12637 (FERM BP-4160); see Japanese Patent Application Laid-Open No. 5-49489

*Corynebacterium acetoacidophilum* AJ 11761 (FERM P-6286); see Japanese Patent Publication No. 2-11235

*Corynebacterium acetoacidophilum* AJ 12638 (FERM P-12382); see Japanese Patent Publication No. 2-11235

(xii) Hosts preferred for producing L-glutamine:

*Brevibacterium flavum* AJ 12418 (FERM BP-2205); see U.S. Pat. No. 5,294,547

*Corynebacterium acetoacidophilum* AJ 12419 (FERM BP-2206); see U.S. Pat. No. 5,294,547

(xiii) Hosts preferred for producing 5'-inosinic acid:

*Brevibacterium ammoniagenes* AJ 12192 (FERM P-7949); see Japanese Patent Publication No. 5-998

*Corynebacterium equi* AJ 11347 (FERM P-4968); see Japanese Patent Publication No. 57-22558

*Corynebacterium equi* AJ 11350 (FERM P-4971); see Japanese Patent Publication No. 57-22558

*Corynebacterium equi* AJ 11352 (FERM P-4973); see Japanese Patent Publication No. 57-22558

All of the above Japanese Patent Publications, Japanese Applications and U.S. Patents are incorporated herein by reference.

To introduce the vector or recombinant DNA comprising a gene coding for a protein having sucrase activity into the above-mentioned Coryneform bacteria, well-known methods such as the protoplast method (Gene, Vol. 39, pp.281-286 (1985) incorporated herein by reference), an electroporation method (Bio/Technology, Vol. 7, pp. (1989); Japanese Patent Application Laid-Open No. 2-207791 incorporated herein by reference), etc. can be used.

The method for culturing the above-mentioned hosts harboring the vector or recombinant DNA need not be different from conventional methods for culturing general L-amino acid-producing microorganisms. For instance, the media to be used for the cultivation may be any conventional one containing carbon sources, nitrogen sources, inorganic ions and, if desired, organic minor nutrients such as amino acids, vitamins, etc.

Typical carbon sources include glucose, sucrose, etc., as well as liquid hydrolysates of starch, molasses, etc., containing them. However, the advantage of the present invention is made clear when cultivation is performed in a medium containing sucrose as the carbon source. That is, the production speed of L-amino acids and nucleic acids is remarkably increased as compared with prior methods when raw materials containing sucrose such as cane molasses and beet molasses are fermented. As the nitrogen sources, ammonia gas, aqueous ammonia, ammonium salts, etc. may be used. When nutritional mutant strains which require amino acids, etc. are used as the hosts, it is necessary to add nutrients such as amino acids, etc. which are required by the strains to the media to be used for culturing them.

The cultivation is preferably performed aerobically, while controlling the pH of the culture between 6.0 and 8.0 and the fermentation temperature between 25° C. and 40° C., until the production and the accumulation of the intended L-amino acid or nucleic acid are substantially stopped. To collect the L-amino acid or nucleic acid thus accumulated in the culture, any ordinary method may be used such as crystallization, ion-exchange methods, etc.

The present invention will now be further described by reference to the following examples. The invention is not limited thereto, however.

EXAMPLE 1

Construction of Gene Library

Chromosomal DNA was prepared from Brevibacterium lactofermentum ATCC 13869, according to a Saito-Miura method (Biochem. Biophs. Acte., Vol. 8278, pp. 619–629 (1963) incorporated herein by reference). About 100 μg of the thus-prepared DNA was partially digested with Sau3Al and charged into a sucrose density gradient of from 10% to 40% and subjected to ultra-centrifugation at 22,000 rpm for 22 hours at 20° C. The bottom of the tube was punctured with a needle, through which one ml aliquots were fractionated to obtain a fraction having approximately from 1500 to 6000 bp (base pairs). This fraction was dialyzed against TE buffer (10 mM Tris, 1 mM EDTA, pH 8.0) and ligated with vector pUC18 that had been cut with BamHl, using T4DNA ligase. Escherichia coli JM 109 was transformed by the resulting DNA. As a result, a gene library comprising about 10,000 clones was constructed.

Designation of Probes

The base sequences of the genes of sucrase, levanase and invertase mentioned below have already been determined. These include levanase (Mol. Genet., Vol. 208, pp. 177–184 (1987) incorporated herein by reference) and sucrase (Gene, Vol. 45, pp. 221–225 (1986) incorporated herein by reference), all derived from Bacillus subtilis; sucrase derived from Streptococcus mutans (Infect. Immun., Vol. 56, pp. 1956–1960 (1988) incorporated herein by reference); invertase derived from Saccharomyces cerevisias (Nucleic Acids Res., Vol. 11, pp. 1943–1954 (1983) incorporated herein by reference); sucrase derived from Zymomonas mobilis (J. Bacteriol., Vol. 172 (1990), pp. 6727–6735 incorporated herein by reference); and sucrase derived from Vibrio algi-nolyticus (Gene, Vol. 80, pp. 49–56 (1989), incorporated herein by reference). The sequences of these genes are partly homologous to one another (J. Bacteriol., Vol. 172, pp. 6727–6735 (1990) incorporated herein by reference). Based on this information, DNAs each having the base sequence selected from SEQ ID NOs: 1, 2 and 3 were designed and synthesized, using a DNA synthesizer, to be used as probes.

Hybridization

The library formed above was used for colony hybridization to screen for colonies hybridizing with the probes, according to a Derek method (FOCUS, Vol. 6, pp. 1–4 (1984) incorporated herein by reference). The temperature for the hybridization was 50° C. and that for washing the filters was 48° C. The clone hybridizing with each probe was cultured in 100 ml of an M9 medium (Molecular Cloning, 2nd Ed., Cold Spring Harbor Press (1989); Maniatis, et al-, A.3 in Appexndixes incorporated herein by reference). The collected cells were washed with 0.9 % physiological saline solution, then suspended in 5 ml of 0.1 M sodium phosphate buffer (pH 7.3) and thereafter disrupted by ultrasonication.

The suspension was then centrifuged at 33,000 rpm for one hour to separate the resulting supernatant and provide a crude extract. 150 μl of the crude extract were mixed with 50 μl of 0.5 M sucrose and reacted at 30° C. for one hour, and then heated at 100° C. for 3 minutes to inactivate the enzyme. The glucose produced was detected, using the Glucose C Test Wako (made by Wako Pure Chemicals Co.), to determine the sucrase activity. The strain of one clone detected with the probe having the sequence of SEQ ID NO:2 showed a strong sucrase activity (Table 1). Table 1 shows the sucrase activity (as relative activity) per mg of the protein. One unit is defined as the activity necessary to produce 1 mg of glucose in one minute at 30° C. The plasmid in the strain providing the sucrase activity is referred to as pBS3-43.

TABLE 1

| Plasmid/Host | Sucrase Activity (unit/mg protein) |
| --- | --- |
| pUC18/JM109 | 0 |
| pBS3-43/JM109 | 3.1 |

Analysis of Clone

The SmaI fragment of about 6 kb was cleaved out of the inserted DNA and this was inserted into the SmaI site of pSAC4, a shuttle vector for Escherichia coli and Coryneform bacteria which imparts resistance to chloramphenicol to the host. The resulting plasmid (pSSM30) expressed sucrase activity both in Escherichia coli and in Brevibacterium lactofermentum. Escherichia coli JM109 having plasmid pSSM30 was named as AJ13047 and deposited under the Budapest Treaty in the National Institute of Bioscience and Human-Technology, Agency of Industrial Science and Technology, 1-3, Higashi 1 chome, Tsukuba-shi, Ibarakiken 305, Japan, to which the deposition number of FERM BP-4800 was rendered.

Determination of Base Sequence

About 7 kb of the DNA fragments including the above-mentioned SmaI fragment which was inserted into pSSM30 were sequenced by a fluorescent labeling method to determine their base sequence. The sequence is represented by SEQ ID NO:4. There were four open reading frames in the sequence (ORF-Fi: from 342nd to 1,505th., ORF-F2: from 2,338th to 3,609th; ORFF3: from 4,438th to 5,358th; ORF-F4: from 5,570th to 6,577th). By the homology between the gene and a known sucrase gene, the structural gene of sucrase was presumed to be ORF-F2, coding for 424 amino acid residues. The other presumed open reading frames were examined to detect the homology, if any, by protein data base NBRF, and the results shown in Table 2 were obtained. ORF-F3 and ORF-F4 were found to have high homology therebetween, and there will be some relation between the two.

TABLE 2

| ORF No. | Number of Amino Acids | Name (homologous protein of different kind) | Degree of Homology (%) |
| --- | --- | --- | --- |
| F1 | 388 | N-acetylglucosamine-6-phosphate deacetylase E. coli (382a.a) | 24 |

TABLE 2-continued

| ORF No. | Number of Amino Acids | Name (homologous protein of different kind) | Degree of Homology (%) |
|---|---|---|---|
| F3 | 307 | UDP-N-acetylmuramoylalanyl-D-glutamyl-meso-6-diaminopimelate synthetase B. sub (494a.a) | 36 |
| F4 | 336 | Phospho-N-acetylmuramoyl-pentapeptide-transferase B. sub (324a.a) | 39 |

EXAMPLE 2

(Introduction of sucrase gene plasmid into L-lysine-producing bacteria) Sucrase gene plasmid pSSM30 was prepared from *Escherichia coli* AJ13047 (FERM BP-4800) and introduced into L-lysine-producing bacteria of *Brevibacterium lactofermentum* AJ 11082 (NRRL B-11470), using an electric pulse method (see Japanese Patent Application Laid-Open No. 2-207791 incorporated herein by reference). The cells were grown on an M-CM2G plate (containing 5 g of glucose, 10 g of polypeptone, 10 g of yeast extract, 5 g of NaCl, 0.2 g of DL-methionine and 15 g of agar in one liter of distilled water and having pH of 7.2) containing 5 μg/ml of chloramphenicol, thereby selecting the intended transformant therefrom. The thus obtained transformant was referred to as AJ 11082/pSSM30.

(Production of L-lysine from sucrose, using sucrase gene-amplified bacteria)

AJ 11082 and AJ 11082/pSSM30 were separately cultured in a medium containing sucrose to produce L-lysine by fermentation. The cells were inoculated in a one-liter jar fermenter containing 300 ml of a medium for lysine production containing sucrose as the carbon source (i.e., containing 100 g of sucrose, 55 g of $(NH_4)_2SO_4$, 1 g of $KH_2PO_4$, 1 g of $MgSO_4.7H_2O$, 50 ml of hydrolysate of soybean protein, 10 mg of $FeSO_4.7H_2O$, 10 mg of $MnSO_4.4H_2O$ and 5 mg of nicotinic acid amide in one liter of distilled water) and the cultivation was performed at 31.5° C. and at pH 7.0 (adjusted with ammonia gas) with agitation and aeration. After the sucrose originally added to the medium was wholly consumed by the cells, a mixture comprising 60 g/dl of sucrose and 8 g/dl of ammonium sulfate, that had been sterilized separately, was continuously fed into the fermenter so that the sucrose concentration in the culture was controlled to fall within the range of from 1 g/dl to 3 g/dl. The cultivation was continued until 150 ml of the feed solution was consumed. Table 3 shows the cultivation time and the amount of L-lysine accumulated. Due to the amplification of the sucrase gene, the speed at which L-lysine was produced by fermentation of sucrose was significantly increased. After the cultivation, a crude enzyme was extracted from the cells by a known method and its sucrase activity was measured. This result is also shown in Table 3.

TABLE 3

| Strain | Cultivation Time (hour) | Amount of L-lysine Accumulated (g/dl) | Sucrase Activity (unit/mg protein) |
|---|---|---|---|
| AJ11082 | 65 | 9.5 | 0.35 |
| AJ11082/pSSM30 | 34 | 9.4 | 3.54 |

EXAMPLE 3

(Introduction of sucrase gene plasmid into wild strain of *Brevibacterium lactofermentum*)

Sucrase gene plasmid pSSM30 was introduced into a wild strain of *Brevibacterium lactofermentum* ATCC 13869, using an electric pulse method (see Japanese Patent Application Laid-Open No. 2-207791 incorporated herein by reference). The cells were grown on an M-CM2G plate (containing 5 g of glucose, 10 g of polypeptone, 10 g of yeast extract, 5 g of NaCl, 0.2 g of DL-methionine and 15 g of agar in one liter of distilled water and having pH of 7.2) containing 5 μg/ml of chloramphenicol, thereby selecting the intended transformant therefrom. The thus-obtained transformant was referred to as ATCC 13869/pSSM30.

(Production of L-glutamic acid from sucrose, using sucrase gene-amplified bacteria)

ATCC 13869 and ATCC 13869/pSSM30 were separately cultured in mediam containing sucrose to produce L-glutamic acid by fermentation. The cells were inoculated in one-liter jar fermenters containing 300 ml of a medium for the L-glutamic acid production containing sucrose as the carbon source (i.e., containing 100 g of sucrose, 15 g of $(NH_4)_2SO_4$, 2.5 g of $KH_2PO_4$, 0.4 g of $MgSO_4.7H_2O$, 50 ml of hydrolysate of soybean protein, 10 mg of $FeSO_4.7HaO$, 10 mg of $MnSO_4.4H_2O$, 350 μg of thiamine. HCl and 3.5 μg of biotin in one liter of distilled water) and cultured at 31.5° C. and at pH 6.5 (adjusted with ammonia gas) with agitation and aeration. After the sucrose originally added to the medium was wholly consumed by the cells, a mixture comprising 60 g/dl of sucrose and 8 g/dl of ammonium sulfate, that had been sterilized separately, was continuously fed into the fermenter such that the sucrose concentration in the culture was controlled to fall within the range of from 1 g/dl to 3 g/dl. Thus, the cultivation was continued until 150 ml of the feed solution was consumed. Table 4 shows the cultivation time and the amount of L-glutamic acid accumulated. Due to the amplification of the sucrase gene, the speed at which L-glutamic acid was produced by fermentation of sucrose was significantly increased.

TABLE 4

| Strain | Cultivation Time (hour) | Amount of L-glutamic Acid Accumulated (g/dl) |
|---|---|---|
| ATCC13869 | 45 | 10.7 |
| ATCC13869/pSSM30 | 29 | 10.9 |

EXAMPLE 4

(Reduction of sucrase gene fragment)

To identify the region essential for increasing the sucrose-metabolizing speed in pSSM30, the DNA fragment was reduced. A gene fragment of about 1.5 kb containing from SacII site starting from the 2,155th base to BanI site starting from the 3,722nd base in the base sequence of SEQ ID NO:4, which contains ORF-F2 presumed to code for the sucrase activity, was extracted from pSSM30, and its both ends were made blunt using T4 DNA polymerase. This fragment was introduced into the SmaI site of pHSG399, a vector for *E. coli*. In addition, so as to make the plasmid replicable in the cells of Coryneform bacteria, the replication origin of a plasmid of *Corynebacterium glutamicum* was introduced thereinto. Specifically, from plasmid pHC4 (see Japanese Patent Application Laid-Open No. 5-7491 incorporated herein by reference) of *Corynebacterium glutamicum* having a replication origin therein, a DNA fragment of 3 kb containing the replication origin was extracted, and its both ends were made blunt using T4 DNA polymerase, followed by modifying the restriction enzyme sites into BamHI site with linkers. This fragment was inserted into the BamHI site of pHSG399 ligated with the sucrase gene of about 1.5 kb. The thus-constructed plasmid was referred to as pSSM30BS.

EXAMPLE 5

(Introduction of reduced sucrase gene plasmid into L-lysine-producing bacteria)

The reduced sucrase gene plasmid pSSM30BS was introduced into an L-lysine-producing strain of *Brevibacterium lactofermentum* AJ 11082 (NRRL B-11470), using an electric pulse method (see Japanese Patent Application Laid-Open No. 2-207791). The cells were grown on an M-CM2G plate (containing 5 g of glucose, 10 g of polypeptone, 10 Cl of yeast extract, 5 g of NaCl, 0.2 g of DL-methionine and 15 g of agar in one liter of distilled water and having pH of 7.2) containing 5 μg/ml of chloramphenicol, selecting the intended transformant therefrom. The thus-obtained transformant was referred to as AJ 11082/pSSM30BS.

(Production of L-lysine from sucrose, using reduced sucrase gene-amplified bacteria) AJ 11082 and AJ 11082/pSSM30BS were separately cultured in a medium containing sucrose to produce L-lysine by fermentation. The cells were inoculated in a one-liter jar fermenter containing 300 ml of a lysine-producing medium having sucrose as the carbon source (i.e., containing 100 g of sucrose, 55 g of $(NH_4)_2SO_4$, 1 g of $KH_2PO_4$, 1 g of $MgSO_4.7H_2O$, 50 ml of hydrolysate of soybean protein, 10 mg of $FeSO_4.7H_2O$, 10 mg of $MnSO_4.4H_2O$ and 5 mg of nicotinic acid amide in one liter of distilled water) and the cultivation was performed at 31.5° C. and at pH of 7.0 (adjusted with ammonia gas) with agitation and aeration. After the sucrose originally added to the medium was wholly consumed by the cells, a mixture comprising 60 g/dl of sucrose and 8 g/dl of ammonium sulfate, that had been sterilized separately, was continuously fed into the fermenter so that the sucrose concentration in the culture might be controlled to fall within the range of from 1 g/dl to 3 g/dl. Thus, the cultivation was continued until 150 ml of the feed solution was consumed. Table 5 shows the cultivation time and the amount of L-lysine accumulated. Due to the amplification of the sucrase gene, the speed at which L-lysine was produced by fermentation of sucrose was noticeably increased. After the cultivation, a crude enzyme was extracted from the cells and its sucrase activity was measured. This is also shown in Table 5.

TABLE 5

| Strain | Cultivation Time (hour) | Amount of L-lysine Accumulated (g/dl) | Sucrase Activity (unit/mg protein) |
|---|---|---|---|
| AJ11082 | 67 | 9.9 | 0.39 |
| AJ11082/pSSM3 OBS | 35 | 9.5 | 4.10 |

EXAMPLE 6

(Introduction of reduced sucrase gene plasmid into wild strain of *Brevibacterium lactofermentum*)

Reduced sucrase gene plasmid pSSM30BS was introduced into a wild strain of Brevibacterium lactofermentum ATCC 13869, using an electric pulse method (see Japanese Patent Application Laid-Open No. 2-207791). The cells were grown on an M-CM2G plate (containing 5 g of glucose, 10 g of polypeptone, 10 g of yeast extract, 5 g of NaCl, 0.2 g of DL-methionine and 15 g of agar in one liter of distilled water and having pH of 7.2) containing 5 μg/ml of chloramphenicol, thereby selecting the intended transformant therefrom. The thus-obtained transformant was referred to as ATCC 13869/pSSM30BS.

(Production of L-glutamic acid from sucrose, using reduced sucrase gene-amplified bacteria)

ATCC 13869 and ATCC 13869/pSSM30BS were separately cultured in a medium containing sucrose to produce L-glutamic acid by fermentation. The cells were inoculated in a one-liter jar fermenter containing 300 ml of a glutamic acid-producing medium having sucrose as the carbon source (i.e., containing 100 g of sucrose, 15 g of $(NH_4)_2SO_4$, 2.5 g of $KH_2PO_4$, 0.4 g of $MgSO_4.7H_2O$, 50 ml of hydrolysate of soybean protein, 10 mg of $FeSO_4.7H_2O$, 10 mg of $MnSO_4.4H_2O$, 350 μg of thiamine. HCl and 3.5 pg of biotin in one liter of distilled water) and the cultivation was performed at 31.5° C. and at pH of 6.5 (adjusted with ammonia gas) with agitation and aeration. After the sucrose originally added to the medium was wholly consumed by the cells, a mixture comprising 60 g/dl of sucrose and 8 g/dl of ammonium sulfate, that had been sterilized separately, was continuously fed into the fermenter such that the sucrose concentration in the culture was controlled to fall within the range of from 1 g/dl to 3 g/dl. Thus, the cultivation was continued until 150 ml of the feed solution was consumed. Table 6 shows the cultivation time and the amount of L-glutamic acid accumulated. Due to the amplification of the sucrase gene, the speed at which L-glutamic acid was produced by fermentation of sucrose was noticeably increased.

TABLE 6

| Strain | Cultivation Time (hour) | Amount of L-glutamic Acid Accumulated (g/dl) |
|---|---|---|
| ATCC13869 | 43 | 10.2 |
| ATCC13869/pSSM30BS | 30 | 10.3 |

Advantage of the Invention

According to the present invention, a DNA fragment derived from Coryneform bacteria and containing a gene coding for a protein having sucrase activity and a recombinant DNA containing said DNA fragment and capable of gene amplification in Coryneform bacteria are obtained. By introducing said recombinant DNA into Coryneform bacteria, the sucrose-assimilating activity of the bacteria is enhanced. Using the bacteria having an enhanced sucrose-assimilating activity, one obtains a method for efficiently producing L-amino acids and nucleic acids in a short period of time.

This application is based on Japanese Patent Application No. 046836/1992, filed Mar. 4, 1992, incorporated herein in its entirety by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A DNA fragment having a nucleic acid sequence encoding the polypeptide encoded by the nucleic acid sequence from base 2,338 to base 3,609 of SEQ ID NO:4.

2. A DNA fragment according to claim 1, having the sequence from base 2,338 to base 3,609 of base sequence ID NO:4.

3. A vector comprising the DNA fragment as claimed in claim 1 or 2 and capable of gene expression in Coryneform bacteria.

4. A Coryneform bacteria comprising the vector as claimed in claim 3 and capable of producing an L-amino acid or a nucleic acid.

5. A method for producing an L-amino acid or a nucleic acid, which comprises culturing a Coryneform bacteria which overexpresses a nucleic acid sequence encoding the polypeptide encoded by the nucleic acid sequence from base 2,338 to base 3,609 of SEQ ID NO:4 in a liquid medium containing sucrose, and isolating said L-amino acid or nucleic acid from said liquid medium.

6. The method as claimed in claim 5, in which the L-amino acid is L-lysine.

7. The method as claimed in claim 5, in which the L-amino acid is L-glutamic acid.

* * * * *